(12) United States Patent
Morimoto

(10) Patent No.: US 10,398,288 B2
(45) Date of Patent: Sep. 3, 2019

(54) HOOD FOR ULTRASONIC ENDOSCOPE AND ULTRASONIC ENDOSCOPE

(71) Applicant: FUJIFILM Corporation, Tokyo (JP)

(72) Inventor: Yasuhiko Morimoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 510 days.

(21) Appl. No.: 14/854,740

(22) Filed: Sep. 15, 2015

(65) Prior Publication Data

US 2016/0073860 A1   Mar. 17, 2016

(30) Foreign Application Priority Data

Sep. 16, 2014 (JP) .................................. 2014-187816

(51) Int. Cl.
*A61B 1/00* (2006.01)
*A61B 8/00* (2006.01)
(Continued)

(52) U.S. Cl.
CPC ...... *A61B 1/00089* (2013.01); *A61B 1/00082* (2013.01); *A61B 1/018* (2013.01);
(Continued)

(58) Field of Classification Search
CPC ................................................. A61B 1/00089
See application file for complete search history.

(56) References Cited

U.S. PATENT DOCUMENTS 4,991,957 A * 2/1991 Sakamoto ............ A61B 1/0005
356/241.4
6,461,304 B1 * 10/2002 Tanaka ................. A61B 1/0008
600/462
(Continued)

FOREIGN PATENT DOCUMENTS

CN   103908305 A   7/2014
JP   2009-268751 A   11/2009
(Continued)

OTHER PUBLICATIONS

Chinese Office Action and Search Report for counterpart Chinese Application No. 201510582508.1, dated Apr. 22, 2019, with English translation.

*Primary Examiner* — Katherine L Fernandez
*Assistant Examiner* — Michael S Kellogg
(74) *Attorney, Agent, or Firm* — Birch, Stewart, Kolasch & Birch, LLP

(57) ABSTRACT

The present invention provides a hood for an ultrasonic endoscope and an ultrasonic endoscope that prevent a body wall from getting into close contact with an observation window at a time such as when an ultrasonic transducer is brought into close contact with the body wall. In a hood for an ultrasonic endoscope to be attached to the ultrasonic endoscope, a notch is formed at a front edge of the hood, and a front edge corner at an observation window side along the notch is provided as an eaves-shaped part. The eaves-shaped part protrudes in front of the observation window, and when an ultrasonic transducer is brought into close contact with the body wall, the eaves-shaped part lies between the body wall and the observation window, thereby preventing the body wall from getting into close contact with the observation window.

11 Claims, 20 Drawing Sheets

(51) Int. Cl.
*A61B 8/12* (2006.01)
*A61B 1/018* (2006.01)

(52) U.S. Cl.
CPC .............. *A61B 8/12* (2013.01); *A61B 8/4272* (2013.01); *A61B 8/445* (2013.01); *A61B 8/44* (2013.01); *A61B 8/4444* (2013.01); *A61B 8/4455* (2013.01)

(56) References Cited

U.S. PATENT DOCUMENTS

| | | | |
|---|---|---|---|
| 2003/0191365 A1* | 10/2003 | Kobayashi | A61B 1/00089 600/127 |
| 2004/0260149 A1* | 12/2004 | Ishibiki | A61B 1/00089 600/127 |
| 2004/0267092 A1* | 12/2004 | Ishibiki | A61B 1/00089 600/127 |
| 2007/0203395 A1* | 8/2007 | Mikkaichi | A61B 1/00087 600/127 |
| 2009/0281429 A1* | 11/2009 | Nishina | A61B 1/00089 600/459 |
| 2012/0232336 A1* | 9/2012 | Kitano | A61B 1/00087 600/102 |
| 2013/0217963 A1* | 8/2013 | Naito | A61B 1/0016 600/104 |

FOREIGN PATENT DOCUMENTS

| | | | |
|---|---|---|---|
| JP | 2013-192798 A | 9/2013 | |
| JP | 2013192798 A * | 9/2013 | ......... A61B 1/00064 |

* cited by examiner

HOOD FOR ULTRASONIC ENDOSCOPE AND ULTRASONIC ENDOSCOPE

CROSS-REFERENCE TO RELATED APPLICATIONS

The patent application claims priority under 35 U.S.C. § 119 to Japanese Patent Application No. 2014-187816, filed on Sep. 16, 2014. Each of the above application(s) is hereby expressly incorporated by reference, in its entirety, into the present application.

BACKGROUND OF THE INVENTION

Field of the Invention

The present invention relates to a hood for an ultrasonic endoscope and an ultrasonic endoscope device, and in particular, to a hood for an ultrasonic endoscope and an ultrasonic endoscope that prevent close contact of a body wall (such as a mucous membrane) to an observation window.

Description of the Related Art

As an ultrasonic endoscope, a known one is equipped with an electronic scanning ultrasonic transducer at a distal end part of an insertion part of an endoscope. While an ultrasonic image of a lesion is being obtained by the ultrasonic transducer, some treatment is performed, such as a puncture needle led out from a treatment instrument lead-out port at the distal end part through a treatment instrument channel is pricked to the lesion, and a cell tissue of the lesion is obtained.

In addition, the ultrasonic endoscope is equipped with an imaging device and a lighting device in addition to the ultrasonic transducer, enables observation by an optical image in the same manner with a general endoscope, and can surely guide the puncture needle to a target region by enabling observation of the optical image until the puncture needle is approximated to a body wall and the body wall is punctured.

Japanese Patent Application Laid-Open No. 2009-268751 discloses a hood used for an ultrasonic endoscope. According to the description, a cylindrical hood is attached to a distal end part of the endoscope, and a space surrounded by the hood is sucked by a suction channel in a state where a distal end opening of the hood abuts on an object region. This enables the object region to abut on an ultrasonic vibrator by drawing the object region into the hood, and stabilizes a relative position between the object region and the ultrasonic vibrator.

SUMMARY OF THE INVENTION

Incidentally, when there is a gap between an ultrasonic transducer and a body wall, an ultrasonic wave is reflected at the gap and an image inside a tissue cannot be obtained. Therefore, in order to obtain a distinct ultrasonic image, it is necessary to bring the ultrasonic transducer into close contact with the body wall. At this time, visibility from an observation window may be lost because the body wall also gets into close contact with an outer surface of the observation window. If visibility from the observation window is lost, a puncturing point (pricking point) cannot be visually recognized.

In addition, confirmation of the puncturing point can be also done by using an ultrasonic image without using an optical image, but even in that case, there is a problem of giving an unpleasant impression because the image will be a reddish uncanny image in whole if the body wall gets into close contact with the observation window.

Even in the case of using the hood described in the Japanese Patent Application Laid-Open No. 2009-268751, the hood cannot prevent the body wall from getting into close contact with the observation window, because the object region and the ultrasonic transducer are brought into close contact with each other by sucking the object region into the hood.

The present invention is made in light of such circumstances, and an objective is to provide an ultrasonic endoscope hood and an ultrasonic endoscope that prevent a body wall from getting into close contact with an observation window in a case such as when an ultrasonic transducer is brought into close contact with the body wall.

In order to achieve the objective, a hood for an ultrasonic endoscope according to one aspect of the present invention, which includes an insertion part including a distal end part, an ultrasonic transducer disposed at the distal end part and including a plurality of ultrasonic vibrators, a treatment instrument lead-out port disposed at the distal end part on a proximal end side relative to the ultrasonic transducer and from which a treatment instrument protrudes toward an ultrasonic observation range of the ultrasonic transducer, and an observation window disposed at the distal end part at a position adjacent to the treatment instrument lead-out port, the hood for an ultrasonic endoscope comprising: a hood body which includes an attachment part to be attached to the distal end part, and whose distal end is to be arranged on the proximal end side relative to the ultrasonic transducer; and an eaves-shaped part provided at the hood body and protruding toward a front of the observation window.

According to the present invention, when the ultrasonic transducer is brought into close contact with a body wall, the eaves-shaped part lies between the observation window and the body wall, and thereby close contact of the body wall to the observation window can be prevented. This enables a visual range of the observation window to be secured.

In the hood for an ultrasonic endoscope according to one aspect of the present invention, according to one implementation, the hood body can comprise a notch at a position corresponding to a position where the treatment instrument lead-out port is formed.

This implementation enables the hood body not to block lead-out of the treatment instrument from the treatment instrument lead-out port.

In the hood for an ultrasonic endoscope according to one aspect of the present invention, the eaves-shaped part of one implementation is preferably provided on an opposite side of the treatment instrument lead-out port, with a plane which is parallel to a longitudinal axis of the insertion part and includes an optical axis of the observation window in between.

In the hood for an ultrasonic endoscope according to one aspect of the present invention, according to one implementation, the eaves-shaped part can be formed using a frame member protruding toward the front of the observation window in a state where the hood body is attached to the distal end part.

This implementation can reduce hindrance of the visual range of the observation window.

In the hood for an ultrasonic endoscope according to one aspect of the present invention, according to one implementation, the eaves-shaped part can be composed of a transparent member.

This implementation can reduce hindrance of the visual range of the observation window.

In the hood for an ultrasonic endoscope according to one aspect of the present invention, according to one implementation, the transparent member can be made of silicone rubber or fluorocarbon rubber.

In the hood for an ultrasonic endoscope according to one aspect of the present invention, the eaves-shaped part according to one implementation can be provided at a position not to overlap with the treatment instrument protruding from the treatment instrument lead-out port in an observation field range of the observation window.

This implementation enables reliable observation of the treatment instrument even when the hood body is used.

In the hood for an ultrasonic endoscope according to one aspect of the present invention, according to one implementation, the eaves-shaped part is preferably provided at a position not included in an ultrasonic scanning range of the ultrasonic transducer.

In the hood for an ultrasonic endoscope according to one aspect of the present invention, according to one implementation, the hood for an ultrasonic endoscope can comprise a switching device configured to switch between a first state in which the eaves-shaped part is situated inside the observation field range of the observation window and a second state in which the eaves-shaped part is situated outside the observation field range of the observation window.

This implementation enables keeping the hood body attached to the distal end part of the endoscope without hindering the visual range of the observation window.

In the hood for an ultrasonic endoscope according to one aspect of the present invention, according to one implementation, the eaves-shaped part is urged to a state of shifting from one state to another state of the first state and the second state, and the switching device includes a string member whose one end is coupled with the eaves-shaped part, and the switching device can set the eaves-shaped part to the another state by applying a tensile force to another end of the string member, and set the eaves-shaped part to the one state by removing the tensile force from the another end of the string member.

In the hood for an ultrasonic endoscope according to one aspect of the present invention, according to one implementation, the switching device includes a balloon connected with the eaves-shaped part and a fluid outflow and inflow device configured to make a fluid flow into or out of the balloon, and the switching device can switch the eaves-shaped part to the first state or the second state by inflating or deflating the balloon by the fluid outflow and inflow device.

In the hood for an ultrasonic endoscope according to one aspect of the present invention, according to one implementation, the hood body includes a first body part provided on a proximal end side of the hood body and a second body part provided on a distal end side of the first body part, and the switching device includes a rotating device configured to rotate the second body part around an axis of the hood body relative to the first body part, and can switch the eaves-shaped part to the first state or the second state by rotating the second body part by the rotating device.

In the hood for an ultrasonic endoscope according to one aspect of the present invention, according to one implementation, the hood body includes a first body part provided on a proximal end side of the hood body and a second body part provided on a distal end side of the first body part, and the switching device includes a transferring device configured to transfer the second body part along an axis direction of the hood body relative to the first body part, and can switch the eaves-shaped part to the first state or the second state by transferring the second body part by the transferring device.

An ultrasonic endoscope according to another aspect of the present invention comprises: an insertion part including a distal end part; an ultrasonic transducer disposed at the distal end part and including a plurality of ultrasonic vibrators; a treatment instrument lead-out port disposed on a proximal end side relative to the ultrasonic transducer at the distal end part and from which a treatment instrument protrudes toward an ultrasonic observation range of the ultrasonic transducer; an observation window disposed at the distal end part at a position adjacent to the treatment instrument lead-out port; and a hood for an ultrasonic endoscope to be attached to the distal end part, wherein the hood for an ultrasonic endoscope comprises: a hood body which includes an attachment part to be attached to the distal end part and whose distal end is to be arranged on the proximal end side relative to the ultrasonic transducer; and an eaves-shaped part provided at the hood body and protruding toward a front of the observation window.

According to the present invention, a body wall can be prevented from getting into close contact with the observation window in a case such as when the ultrasonic transducer is brought into close contact with the body wall.

DETAILED DESCRIPTION OF THE EMBODIMENTS

Preferred embodiments of the present invention will be explained in detail below according to the attached drawings.

Figure 1:
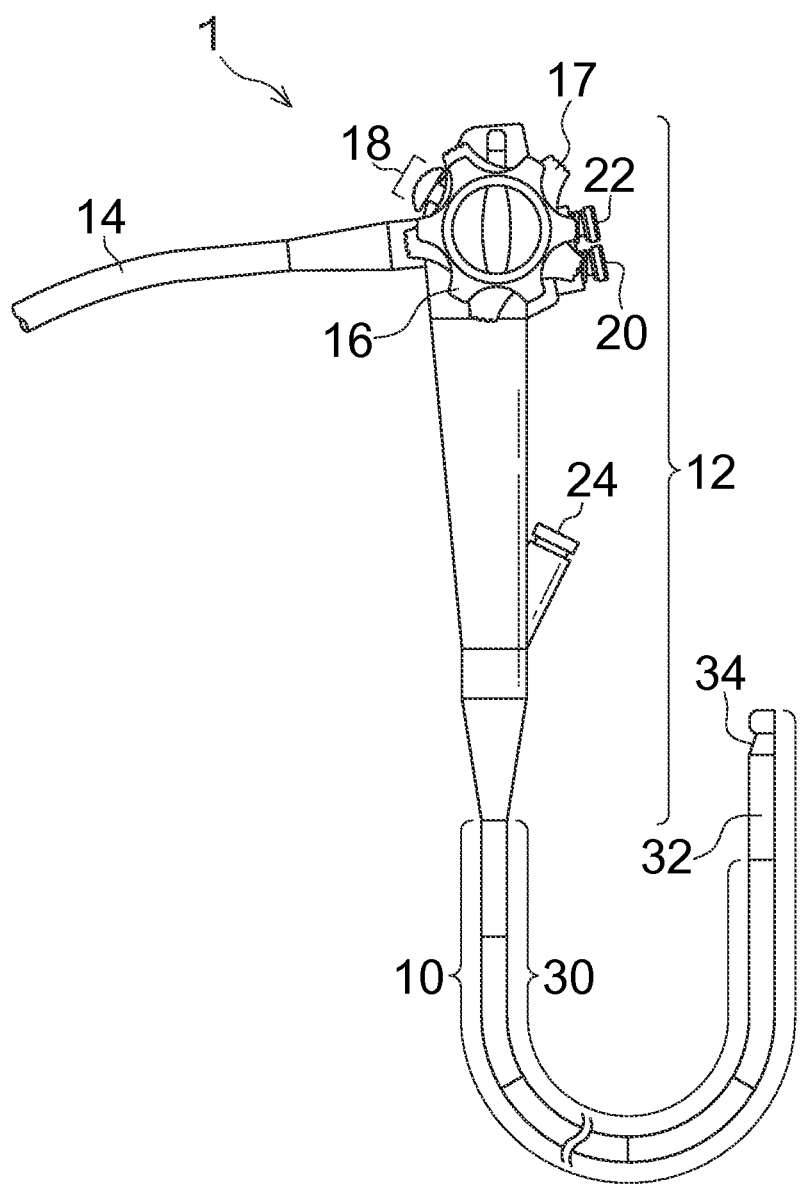
FIG. 1 is an overall view illustrating an example of an ultrasonic endoscope 1 using a hood for an ultrasonic endoscope according to the present invention.

FIG. 1 is an overall view illustrating an example of an ultrasonic endoscope 1 using a hood for an ultrasonic endoscope according to the present invention.

The ultrasonic endoscope 1 (hereinafter simply called an endoscope 1) in the figure comprises: an insertion part 10 inserted into a body of a subject; an operation part 12 provided consecutively on a proximal end side of the insertion part 10 and to let an operator grab it to perform various operations; an unillustrated processor device provided consecutively to the operation part 12 and constituting part of an endoscope system; and a universal cord 14 to connect the endoscope 1 to system component devices such as a light source device.

The insertion part 10 is formed into a shape of being small in diameter and long in length as a whole and comprises, consecutively in the order from a proximal end side to a distal end side, a flexible part 30 having flexibility, a bending part 32 bendable by operation of the operation part 12; and a distal end part 34 where devices such as an imaging device and an ultrasonic transducer (electromagnetic acoustic transducer) are arranged.

The operation part 12 is provided with various operation members operated by the operator, and is provided with, for example, a left-and-right angle knob 16, an up-and-down angle knob 17, an erection operation lever 18, an air-supply and water-supply button 20, and a suction button 22. The bending part 32 bends in a left or right direction and an up or down direction by operation of the left-and-right angle knob 16 and the up-and-down angle knob 17.

In addition, the operation part 12 is provided with a treatment instrument introduction port 24 that lets a treatment instrument go into a treatment instrument insertion path (treatment instrument insertion channel) passing through the inside of the insertion part 10.

The universal cord 14 includes therein an electric cable, a light guide, and a fluid tube. An unillustrated end of the universal cord 14 is provided with a connector. Connecting the connector to prescribed system component devices constituting the endoscope system, such as the processor device and the light source device lets the system component devices supply the endoscope 1 with necessary things to operate the endoscope 1, such as electric power, a control signal, illumination light, liquid and gas, and also lets the endoscope 1 transmit data on an observation image obtained by the imaging device at the distal end part 34 and data on an ultrasonic image obtained by the ultrasonic transducer to the system component devices. Additionally, the observation image and the endoscope image transmitted to the system component devices are displayed on a monitor.

Figure 2:
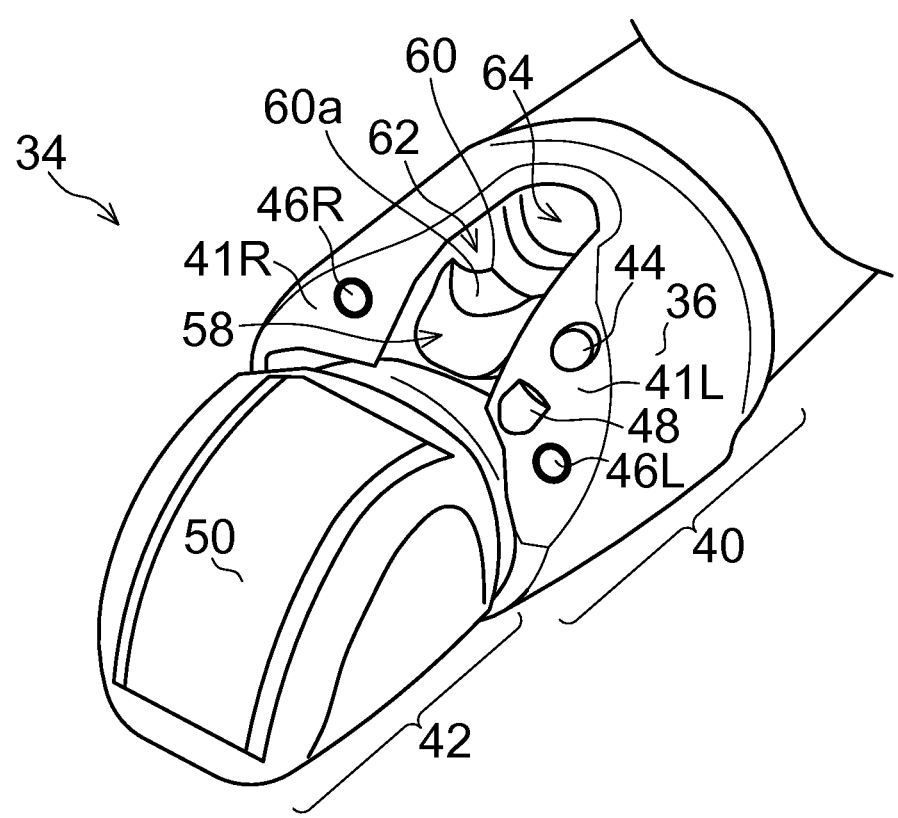
FIG. 2 is a perspective view illustrating an enlarged distal end part.

FIG. 2 is a perspective view illustrating the enlarged distal end part 34. The distal end part 34 as illustrated in the figure includes a base part 40 arranged on a proximal end side and an extended part 42 extending from the base part 40 to a distal end side.

At the extended part 42, a convex ultrasonic transducer 50 is arranged in which a large number of ultrasonic vibrators that transmit and receive ultrasonic waves are set in array along an arcuate ultrasonic transmitting and receiving plane. This enables the ultrasonic transducer 50 to obtain an ultrasonic image (tomographic image) on a scanning surface parallel to an axis of the insertion part 10, and data on the ultrasonic image is transmitted to the system component devices connected with the universal cord 14, via a signal cable passing through the inside of the insertion part 10, the operation part 12, and the universal cord 14.

The base part 40 has an outer circumference surface 36 along a cylinder surface whose center is the axis of the insertion part 10, and on a distal end side of the outer circumference surface 36, a left oblique surface 41L and a right oblique surface 41R which face the distal end side and in an oblique upward direction are provided. On the left oblique surface 41L, an observation window 44, an air/water supply nozzle 48, and an illumination window 46L are provided. On the right oblique surface 41R, an illumination window 46R is provided. At a central part between the left oblique surface 41L and the right oblique surface 41R, a treatment instrument lead-out port 58 is provided.

Inside the base part 40 situated on a proximal end side of the observation window 44, an imaging device made by integrally assembling an imaging optics system and a solid imaging element is arranged. This allows light from an observation region in an observation field (field range) of the imaging device to be taken in from the observation window 44, lets the imaging optics system to form a light image of the observation region, and lets the solid imaging element to convert the light image into an electric signal. Then, data on the observation image which has been converted into the electric signal is transmitted to the system component devices connected with the universal cord 14, via the signal cable passing through the inside of the insertion part 10, the operation part 12, and the universal cord 14.

A light emission part is arranged inside a part of the base part 40 situated on a proximal end side of each of the illumination windows 46R and 46L. To the light emission part, illumination light is guided from the system component devices connected with the universal cord 14, via the light guide passing through the inside of the insertion part 10, the operation part 12, and the universal cord 14, and the illumination light is emitted from the light emission part and illuminates the observation region via the illumination windows 46R and 46L.

The air/water supply nozzle 48 is connected with the system component devices connected with the universal cord 14, via a fluid tube passing through the inside of the insertion part 10, the operation part 12, and the universal cord 14, and gas or water supplied by the system component devices is ejected toward the observation window 44 from the air/water supply nozzle 48, and thereby cleaning or the like of the observation window 44 is performed. In addition, air supply or water supply from the air/water supply nozzle 48 is performed based on operation of the air-supply and water-supply button 20 in the operation part 12.

The treatment instrument lead-out port 58 has a concave treatment instrument erection space 62 which is recessed than a vicinity of that space 62, and an opening 64 of the treatment instrument insertion channel is arranged on a proximal end side of the treatment instrument erection space 62.

The opening 64 is linked to the treatment instrument introduction port 24 of the operation part 12 through the treatment instrument insertion channel (treatment instrument insertion path) passing through the inside of the insertion part 10, and the treatment instrument inserted from the treatment instrument introduction port 24 is led out to the treatment instrument erection space 62 from the opening 64.

In addition, a treatment instrument erection stand 60 (hereinafter simply called an erection stand 60) is arranged in a distal end side of the opening 64 in the treatment instrument erection space 62.

The erection stand 60 includes a concave guide surface 60a curved upward from a proximal end side to a distal end side, on an upper surface side of the erection stand 60, and the treatment instrument led out from the opening 64 abuts on the guide surface 60a of the erection stand 60 and bends upward. Therefore, the treatment instrument led out from the treatment instrument lead-out port 58 of the distal end part 34 is arranged by the erection stand 60 such that the treatment tool protrudes along an upward oblique direction toward the distal end side from the proximal end side relative to a central axis (longitudinal axis of the insertion part 10) passing through the center of the distal end part 34.

The erection stand 60 is linked to the erection operation lever 18 of the operation part 12 via an operation wire passing through the inside of the insertion part 10, and moves to a direction where the erection stand 60 stands up or falls down by operation of the erection operation lever 18. Thereby, a standing angle of the erection stand 60 is changed. This changes a lead-out direction (lead-out angle) of the treatment instrument led out from the distal end part 34 (treatment instrument lead-out port 58).

Additionally, a suction channel is linked to the treatment instrument insertion channel, and sucking from the treatment instrument lead-out port 58 is turned on or off by operation of the suction button 22 of the operation part 12.

Next, a hood for an ultrasonic endoscope to be detachably attached to the distal end part 34 of the endoscope 1 will be explained.

Figure 3:
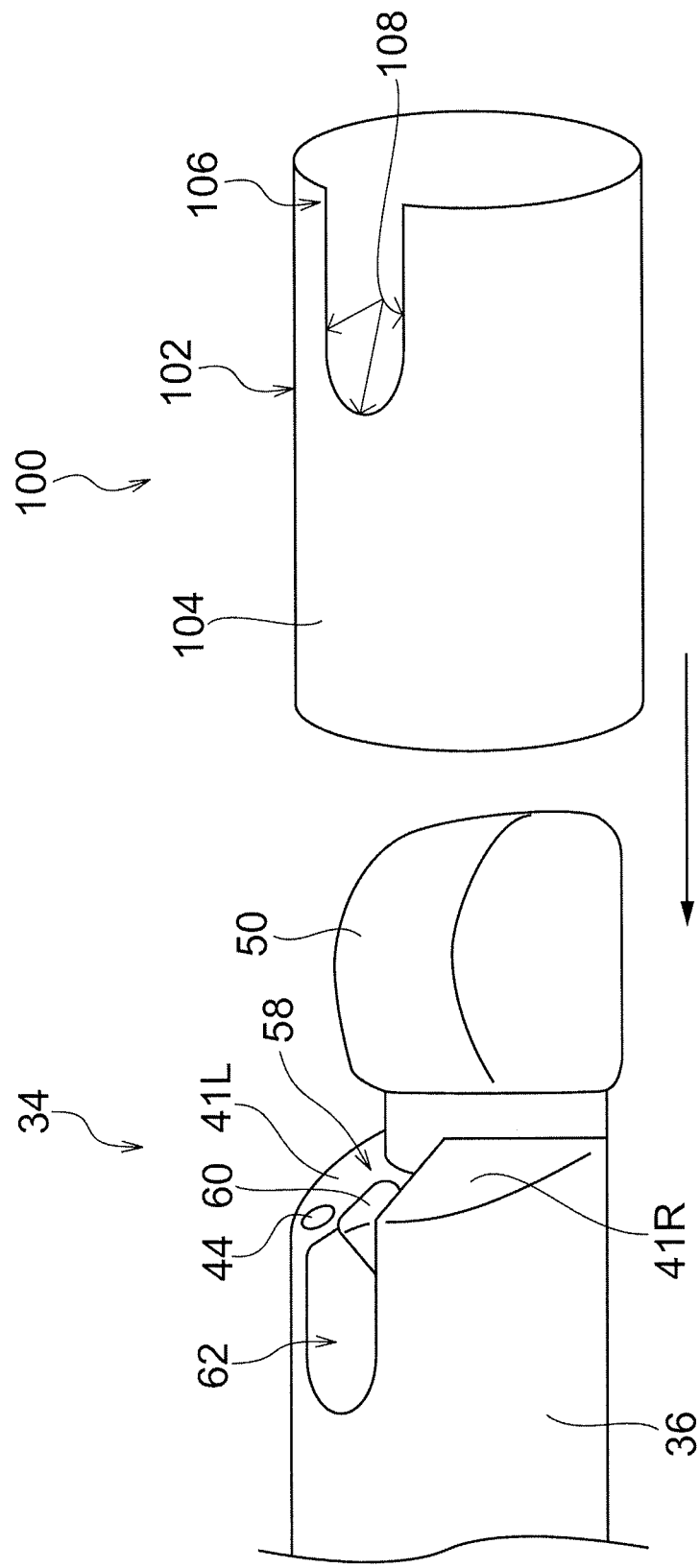
FIG. 3 is a perspective view illustrating an endoscope and a distal end part, and a hood for an ultrasonic endoscope in a first embodiment in a detached state.
Figure 4:
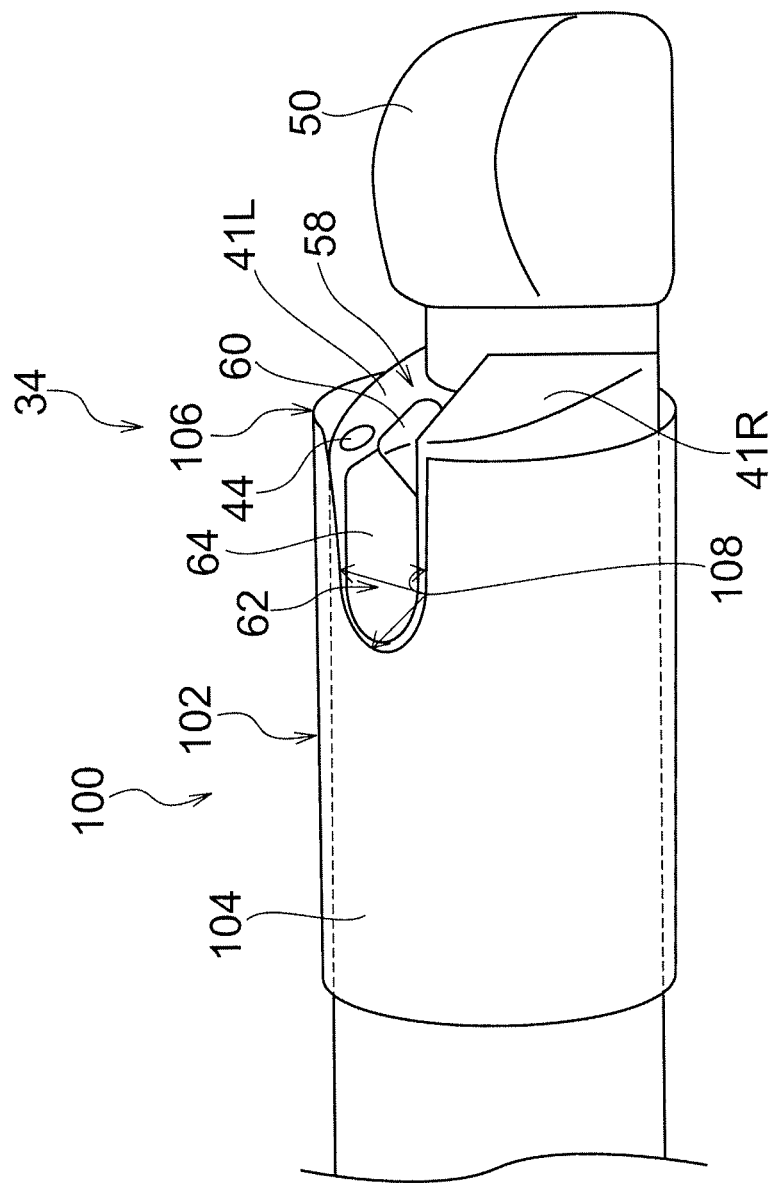
FIG. 4 is a perspective view illustrating the endoscope and the distal end part, and the hood for an ultrasonic endoscope in the first embodiment in an attached state.

FIG. 3 illustrates the distal end part 34 of the endoscope 1 and a hood for an ultrasonic endoscope 100 (hereinafter simply called a hood 100) in a first embodiment, and is a perspective view illustrating a state where the hood 100 is detached from the distal end part 34. FIG. 4 is a perspective view illustrating a state where the hood 100 is attached to the distal end part 34.

The hood 100 illustrated in these figures includes: a hood body 102 which is formed in a cylindrical shape by a frame member and an elastic material such as, for example, silicone rubber or fluorocarbon rubber; and a notch 108 extending from a distal end to a proximal end side. However, the hood 100 may be not necessarily transparent.

An inner circumference surface of the hood body 102 has approximately the same diameter as the cylindrical outer circumference surface 36 of the distal end part 34, the hood body 102 fits onto the outer circumference surface 36 of the distal end part 34 as in FIG. 4, and the inner circumference surface on a proximal end side of the hood body 102 gets into close contact with the outer circumference surface 36 of the distal end part 34. This makes the hood 100 (hood body 102) attached to the distal end part 34 as in FIG. 4.

Additionally, a part of the hood body 102 on a proximal end side relative to a proximal end of the notch 108 has a function as an attachment part 104 to attach the hood body 102 to the distal end part 34. A configuration of the attachment part 104 can be changed into any other arbitrary configuration. Any fixing means such as adhesive or an adhesive tape can be used for attaching the hood body 102 to the distal end part 34.

In addition, the hood body 102 is attached at a position where a position of the base end of the notch 108 nearly accords with a position of a base end of the concave treatment instrument erection space 62 at the treatment instrument lead-out port 58 of the distal end part 34, and a position in a circumferential direction of the treatment instrument erection space 62 nearly accords with a position in a circumferential direction of the notch 108. Thus, the hood body 102 is fixed to the distal end part 34 at an almost prescribed position and arranged at a position where the hood body 102 does not block (obstruct) lead-out of the treatment instrument from the treatment instrument lead-out port 58.

When the hood body 102 is attached to the distal end part 34 in this manner, the distal end of the hood body 102 is arranged on the proximal end side relative to the ultrasonic transducer 50.

In addition, at least distal parts of both right and left sides of the notch 108 of the hood body 102 is arranged so as to be apart from the left oblique surface 41L and the right oblique surface 41R which face the distal end side and in an oblique upward direction (inclined at a slant) in at the distal end part 34, and in a state where hood body 102 is not in contact with any surface on the distal end part 34.

Figure 5:
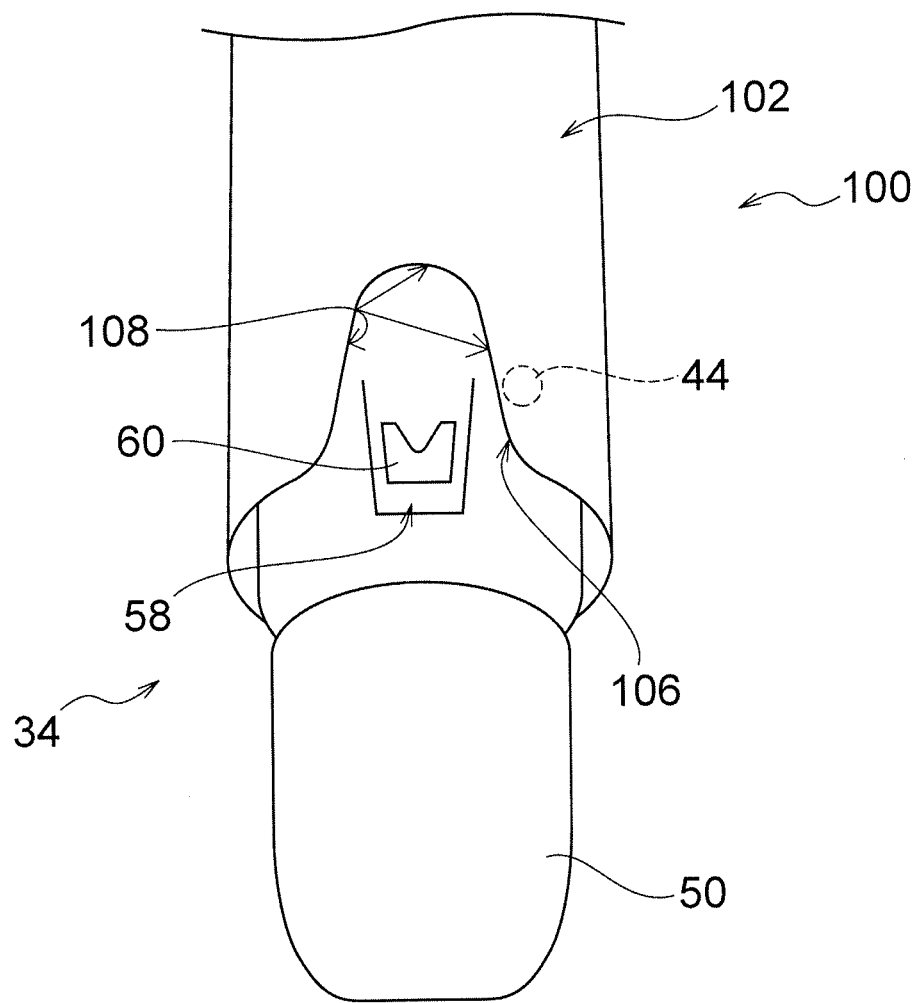
FIG. 5 is a diagram illustrating the distal end part viewed from a front side of an observation window.

Then, the eaves-shaped part 106 which is a distal end side part in a left side of the notch 108 of the hood body 102 is arranged on the left oblique surface 41L of the distal end part 34 so as to protrude toward the front of the observation window 44 which faces the distal end side and in the oblique upward direction. In other words, the eaves-shaped part 106 of the hood body 102 protrudes to a position overlapping with a position of the observation window 44 in a figure illustrating the distal end part 34 from the front side of the observation window 44 as in FIG. 5.

Figure 6:
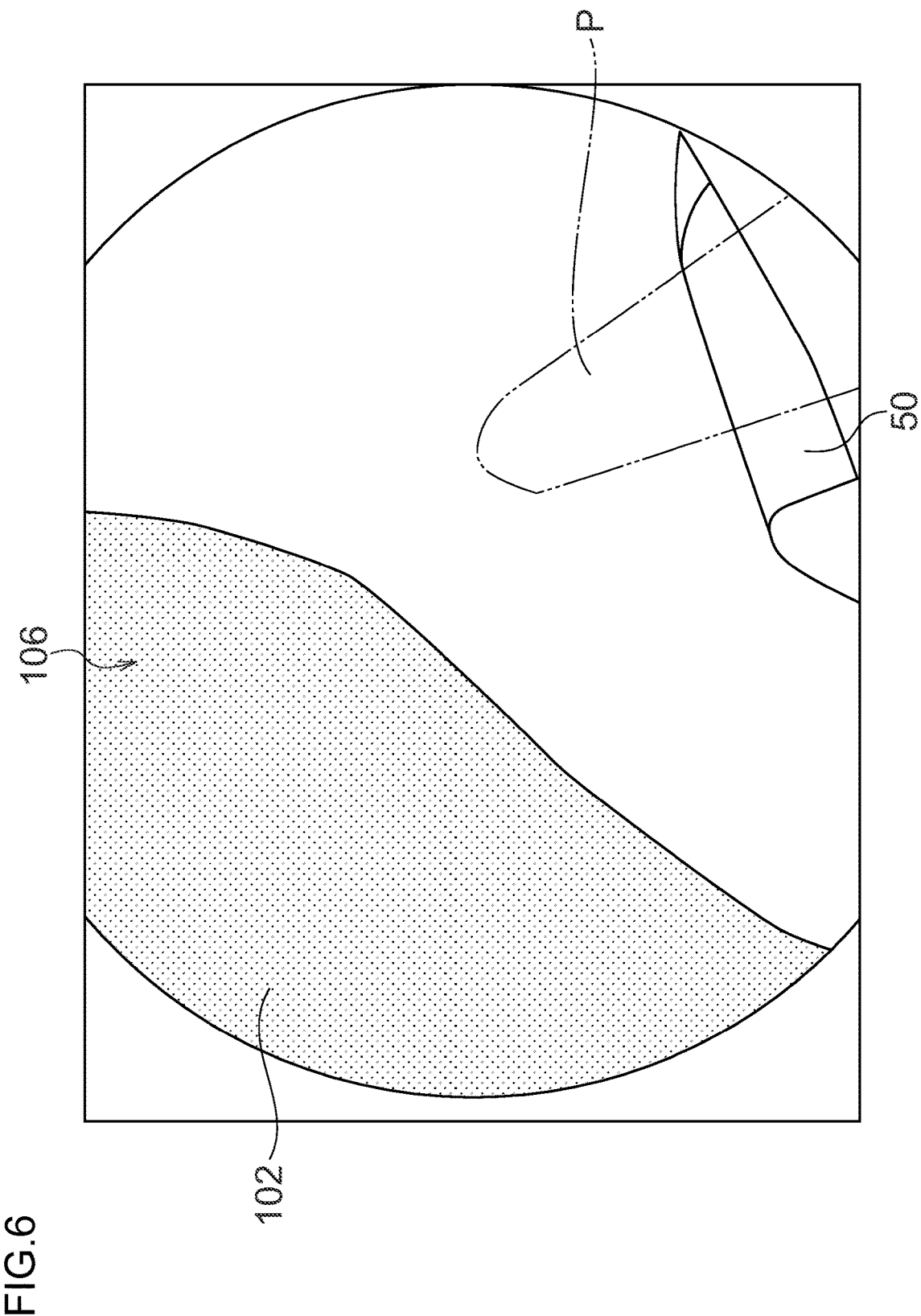
FIG. 6 is a diagram illustrating an image taken in a state in which the hood in the first embodiment is attached to the distal end part.

Furthermore, FIG. 6 illustrates an image taken by the imaging device via the observation window 44 in the state of the hood 100 being attached to the distal end part 34, and the eaves-shaped part 106 is arranged at a position not overlapping with a treatment instrument P protruding from the treatment instrument lead-out port 58 in the observation field range of the observation window 44 (imaging device) as illustrated in the figure.

Additionally, it is desirable that the eaves-shaped part 106 is provided on an opposite side of the treatment instrument lead-out port 58 with respect to a plane parallel to the axis (longitudinal axis) of the insertion part 10 and including the optical axis of the observation window 44 in between, or it is desirable that the eaves-shaped part 106 is provided at a position not included in an ultrasonic scanning range of the ultrasonic transducer 50, and it is more desirable that the eaves-shaped part 106 is provided at a position which satisfies both.

Figure 7:
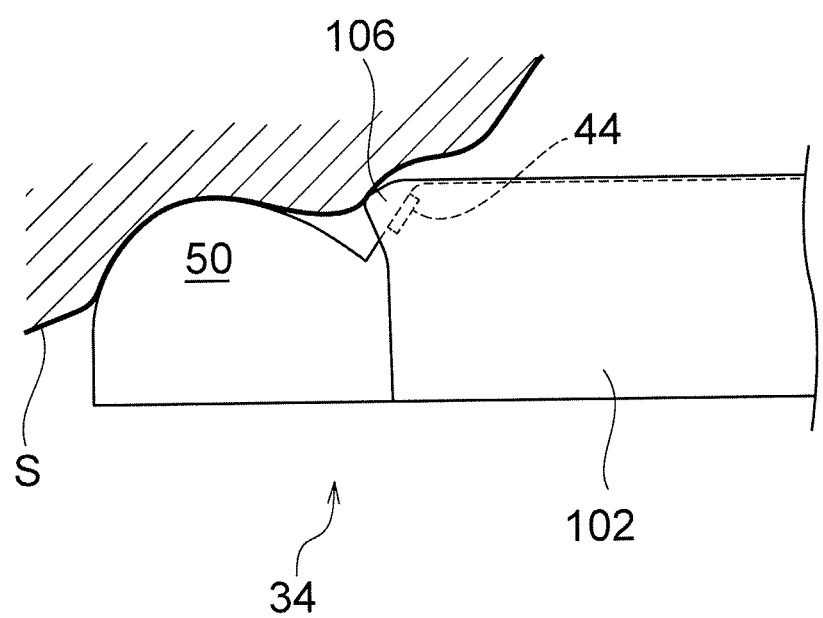
FIG. 7 is a diagram illustrating a state when an ultrasonic image is obtained by bringing an ultrasonic transducer into close contact with a body wall.

According to the hood 100 in the first embodiment, in the case where the ultrasonic transmitting and receiving plane of the ultrasonic transducer 50 is brought into close contact with a body wall S as in FIG. 7 at a time of acquisition of an ultrasonic image when a puncture needle is pricked or the like, the eaves-shaped part 106 of the hood 100 lies between the observation window 44 and the body wall S. Therefore, the body wall S is prevented from getting into close contact with the observation window 44.

Next, a hood for an ultrasonic endoscope 150 (hereinafter simply called a hood 150) in a second embodiment will be explained.

Figure 8:
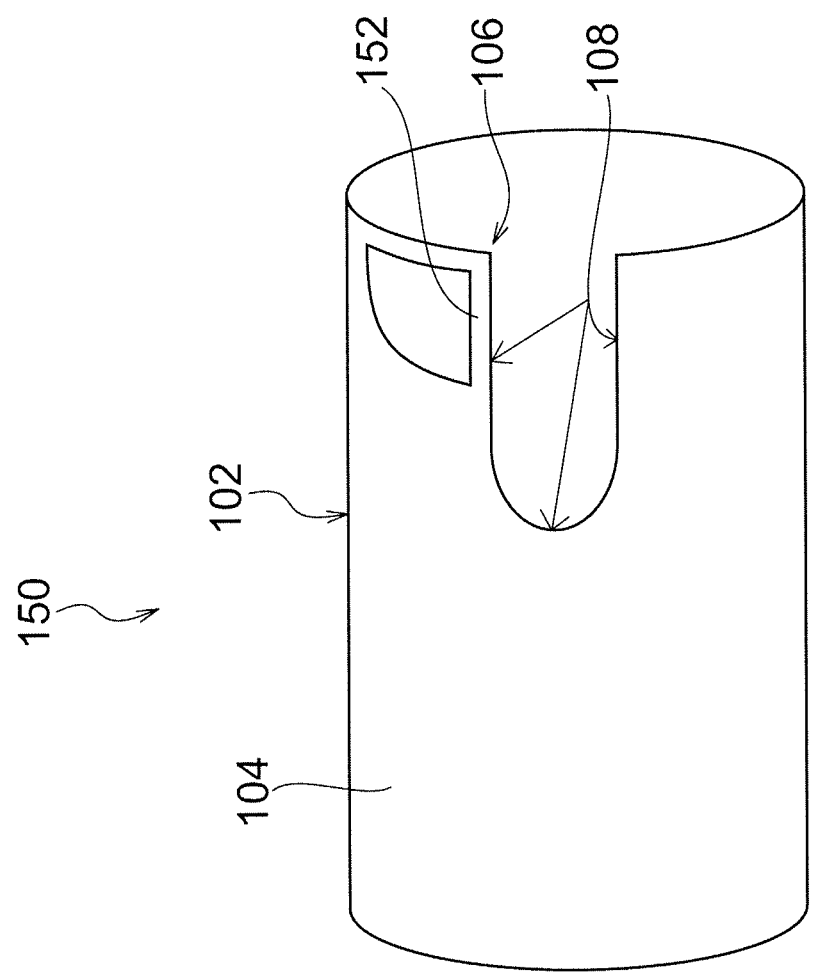
FIG. 8 is a perspective view illustrating a hood for an ultrasonic endoscope in a second embodiment.

FIG. 8 is a perspective view illustrating the hood 150 in the second embodiment. Additionally, the same part as or a similar function part to the hood 100 in the first embodiment is given the same reference numeral and its explanation will be omitted.

As illustrated in the figure, in the hood 150 in the second embodiment, at least the eaves-shaped part 106 is composed of a frame member 152, and the frame member 152 at the eaves-shaped part 106 protrudes toward in front of the observation window 44 in a state of the hood 150 (hood body 102) being attached to the distal end part 34.

According to the hood 150 in the second embodiment, in the same manner as the hood 100 in the first embodiment, when the ultrasonic transmitting and receiving plane of the ultrasonic transducer 50 is brought into close contact with a body wall, the frame member 152 of the eaves-shaped part 106 of the hood 150 lies between the observation window 44 and the body wall, and thereby the body wall is prevented from getting into close contact with the observation window 44.

Figure 9:
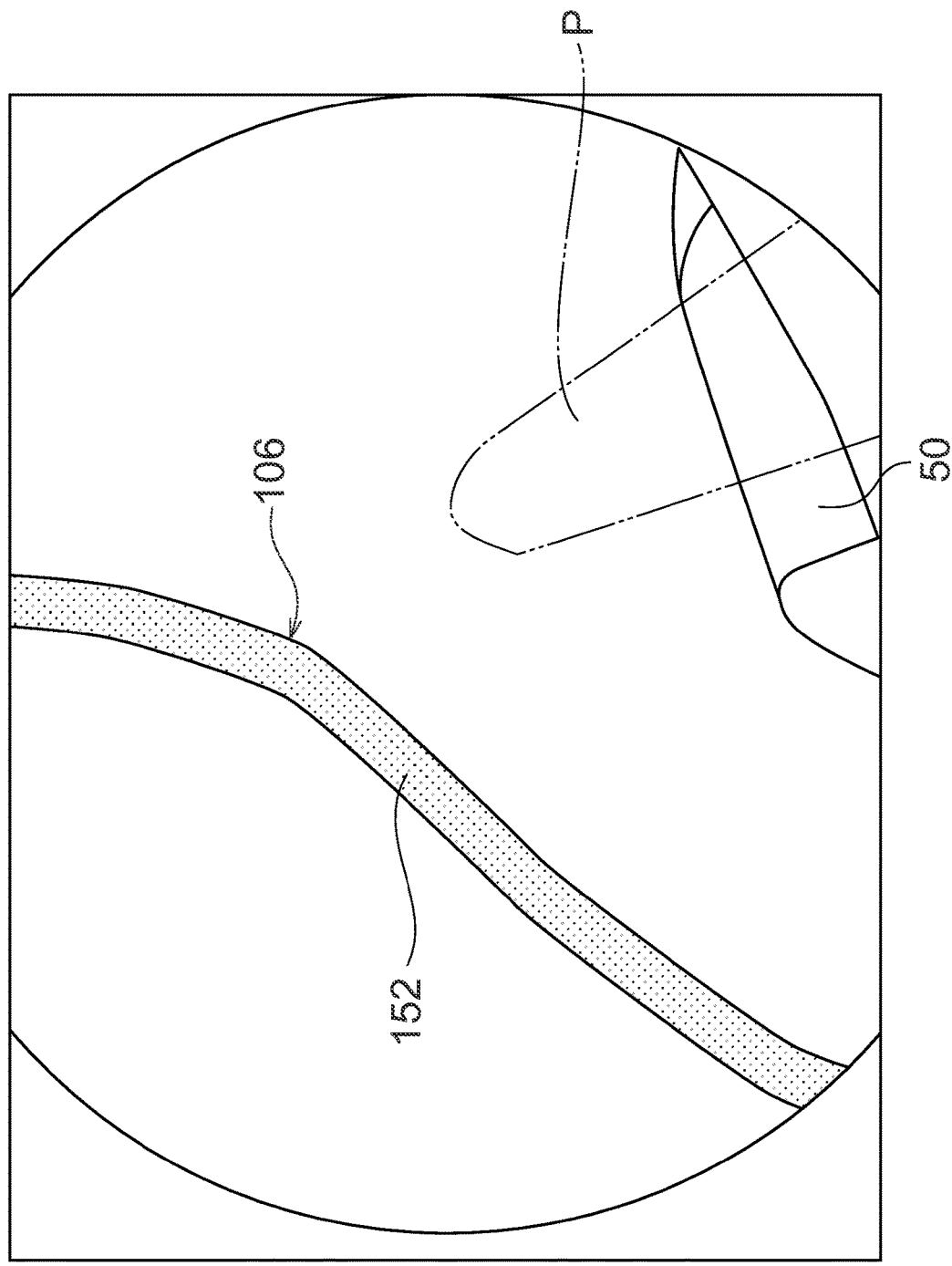
FIG. 9 is a diagram illustrating an image taken in a state in which the hood in the second embodiment is attached to the distal end part.

In addition, FIG. 9 illustrates an image taken by the imaging device via the observation window 44 in the state of the hood 150 being attached to the distal end part 34. As illustrated in the figure, regarding the hood 150, the eaves-shaped part 106 composed of the frame member 152 is taken in the image. Therefore, the visual range becomes clear.

Next, a hood for an ultrasonic endoscope 200 (hereinafter simply called a hood 200) in a third embodiment will be explained.

Figure 10:
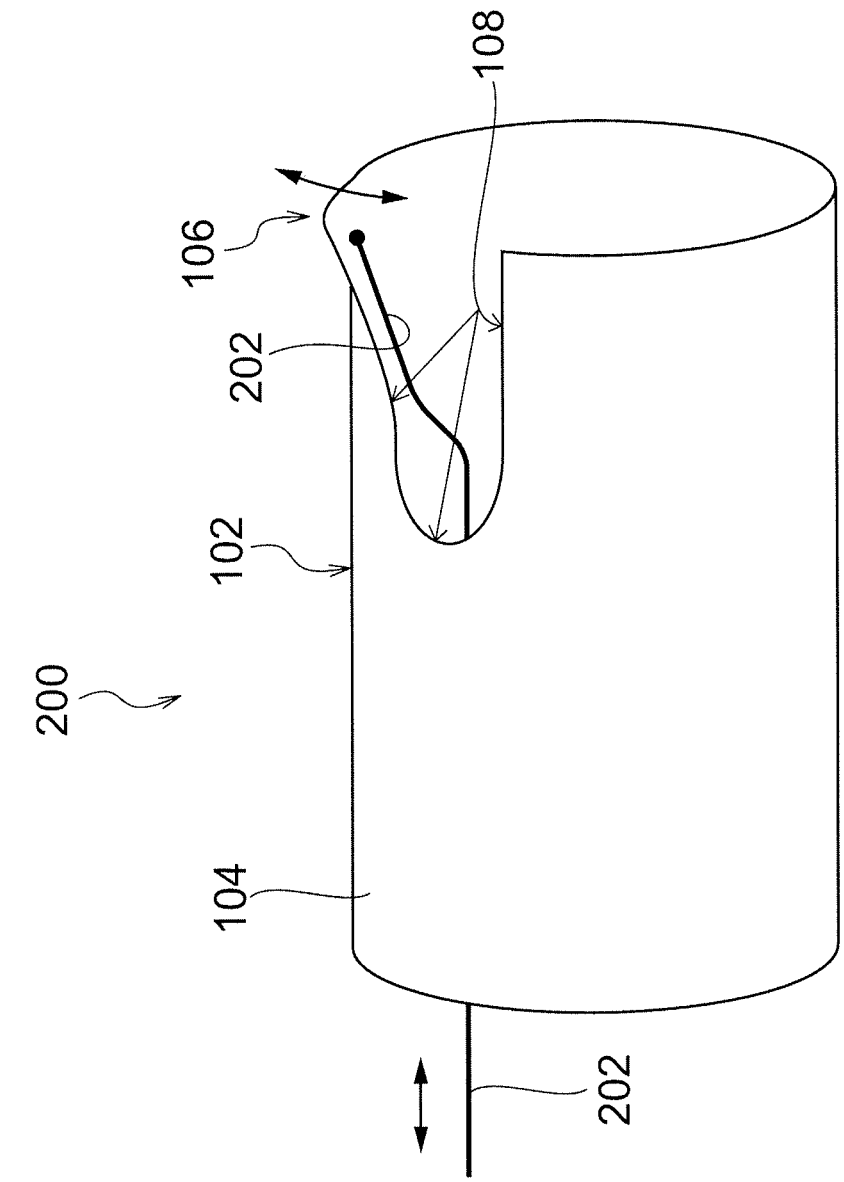
FIG. 10 is a perspective view illustrating a hood in a third embodiment.

FIG. 10 is a perspective view illustrating the hood 200 in the third embodiment. Additionally, the same part as or a similar function part to the hood 100 in the first embodiment is given the same reference numeral and its explanation will be omitted.

As illustrated in the figure, in the hood 200 in the third embodiment, the eaves-shaped part 106 is given a habit (reformed) into a state where the eaves-shaped part 106 deforms toward a radially outside relative to an axis of the hood body 102.

On the other hand, as a switching device, one end of a string member 202 is coupled with the inner circumference surface or the like of the eaves-shaped part 106, and the other end of the string member 202 is led out from, for example, the treatment instrument introduction port 24 of the operation part 12 via the treatment instrument insertion channel from the treatment instrument lead-out port 58.

In this configuration, an operator can apply tensile force to the other end of the string member 202 led out from the treatment instrument introduction port 24. Thereby, the eaves-shaped part 106 deforms toward radially inside relative to the axis of the hood body 102 to be in a first state where the eaves-shaped part 106 is situated inside the observation field range of the observation window 44 (imaging device). When the operator to remove the tensile force from the other end of the string member 202, the state switches to a second state where the eaves-shaped part 106 is situated outside the observation field range of the observation window 44.

Therefore, when the visual range has priority, the eaves-shaped part 106 can be shifted in the second state so that the eaves-shaped part 106 is not reflected in the observation field range of the observation window 44.

Additionally, also in the following description, the first state denotes the state in which the eaves-shaped part 106 is deformed toward radially inside relative to the axis of the hood body 102 and situated inside the observation field range of the observation window 44, and the second state denotes a state in which the eaves-shaped part 106 is situated outside the observation field range of the observation window 44. However, the second state may denote a state in which a size (area) of the eaves-shaped part 106 entering inside the observation field range of the observation window 44 is smaller than that of the first state but not a state in which the eaves-shaped part 106 has completely retreated from the observation field range of the observation window 44.

In addition, an implementation is also easily possible in which applying tensile force to the string member 202 shifts to the second state, and removing the tensile force shifts to the first state. In other words, the hood 200 in FIG. 10 is in a form in which the eaves-shaped part 106 is urged to shift from the first state to the second state, applying tensile force to the string member 202 shifts the eaves-shaped part 106 to the first state, and removing the tensile force from the string member 202 shifts the eaves-shaped part 106 to the second state.

In contrast, the eaves-shaped part 106 is made in the first state, for example, by making the eaves-shaped part 106 in a state of being arranged along the same cylindrical surface as the other part of the hood body 102, or by making the eaves-shaped part 106 in a state of being deformed toward the radial inside relative to the axis of the hood body 102 by giving a habit (reforming) to the eaves-shaped part 106. Then, one end of the string member 202 is coupled with the outer circumference surface or the like of the eaves-shaped part 106. Thereby, by applying tensile force to the string member 202, the eaves-shaped part 106 deforms toward radially outside and the state shifts to the second state. By removing the tensile force from the string member 202, the eaves-shaped part 106 shifts to the first state.

In addition, an implementation is possible in which the string member 202 passes through a part other than the treatment instrument insertion channel.

Next, a hood for an ultrasonic endoscope 250 (hereinafter simply called a hood 250) in a fourth embodiment will be explained.

Figure 11:
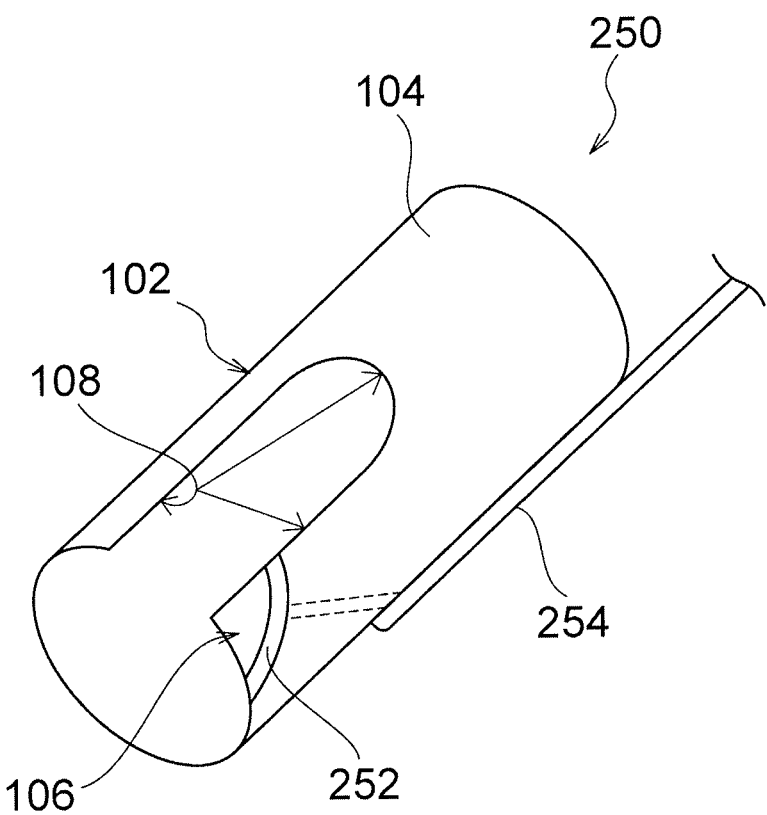
FIG. 11 is a perspective view illustrating a hood in a fourth embodiment.
Figure 12:
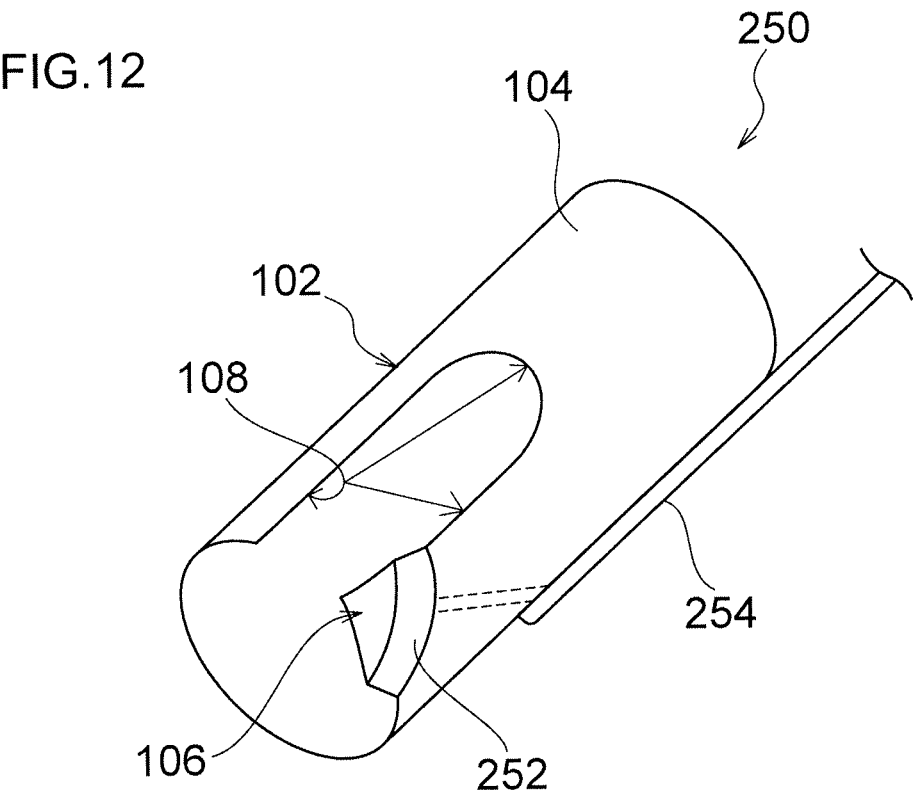
FIG. 12 is a perspective view illustrating the hood in the fourth embodiment.

FIGS. 11 and 12 are perspective views illustrating the hood 250 in the fourth embodiment. Additionally, the same part as or a similar function part to the hood 100 in the first embodiment is given the same reference numeral and its explanation will be omitted.

As illustrated in these figures, the hood 250 in the fourth embodiment includes, as a switching device, an inflatable and deflatable balloon 252 at the eaves-shaped part 106, a fluid supply and discharge tube 254 in communication with the balloon 252, and an unillustrated fluid outflow and inflow device connected with the fluid supply and discharge tube 254.

According to this, supplying fluid (gas or liquid) into the balloon 252 by the fluid outflow and inflow device to inflate the balloon 252 shifts the state to the first state in which the eaves-shaped part 106 is situated inside the observation field range of the observation window 44 as in FIG. 12. In contrast, discharging the fluid from the balloon 252 by the fluid outflow and inflow device to deflate the balloon 252 shifts the state to the second state in which the eaves-shaped part 106 is situated outside the observation field range of the observation window 44 as in FIG. 11.

Therefore, when the visual range of the observation window 44 has priority, the eaves-shaped part 106 can be made in the second state so that the eaves-shaped part 106 is not reflected in the observation field range of the observation window 44.

Next, a hood for an ultrasonic endoscope 300 (hereinafter simply called a hood 300) in a fifth embodiment will be explained.

Figure 13:
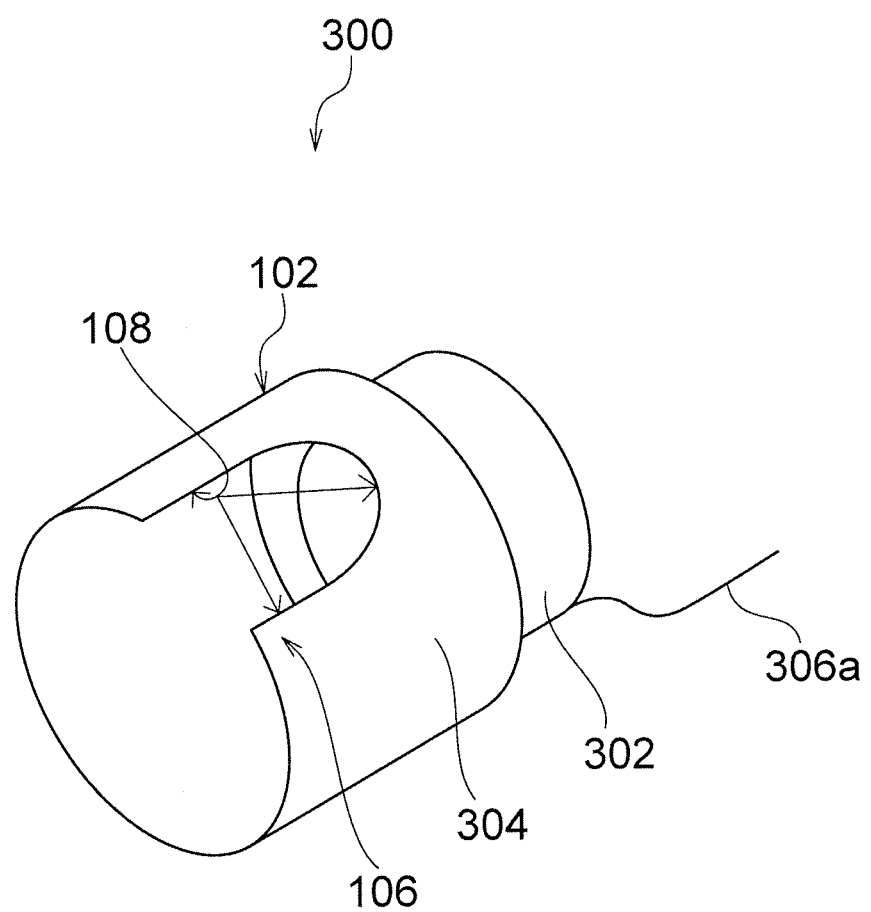
FIG. 13 is a perspective view illustrating a hood in a fifth embodiment.

FIG. 13 is a perspective view illustrating the hood 300 in the fifth embodiment. Additionally, the same part as or a similar function part to the hood 100 in the first embodiment is given the same reference numeral and its explanation will be omitted.

As illustrated in the figure, in the hood 300 in the fifth embodiment, the hood body 102 includes a first body part 302 provided on a proximal end side thereof and a second body part 304 provided on a distal end side of the first body part 302. The second body part 304 is provided with the notch 108 and includes the eaves-shaped part 106. The first body part 302 is to be attached to the distal end part 34.

Figure 14:
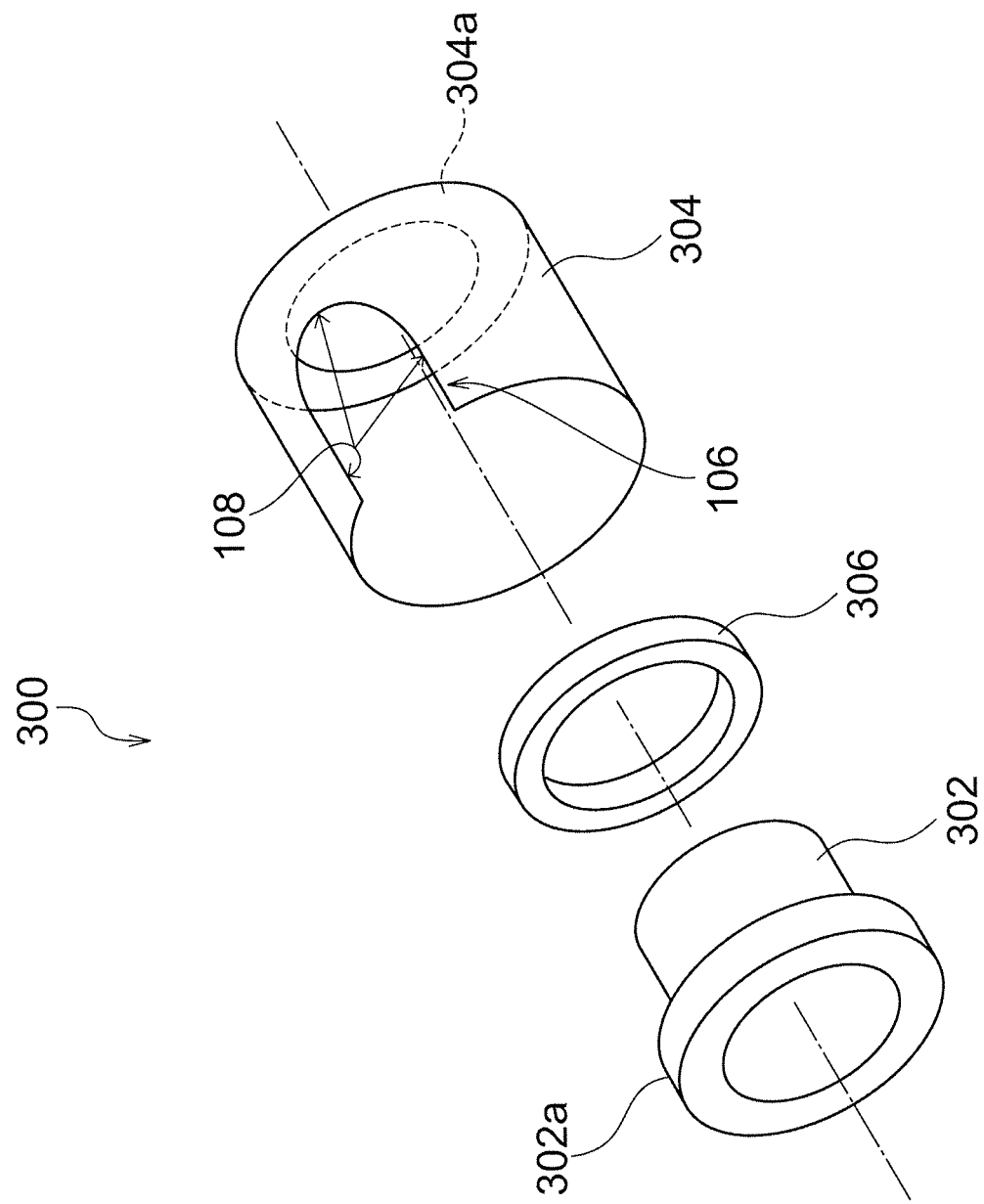
FIG. 14 is an exploded view of the hood in the fifth embodiment.
Figure 15:
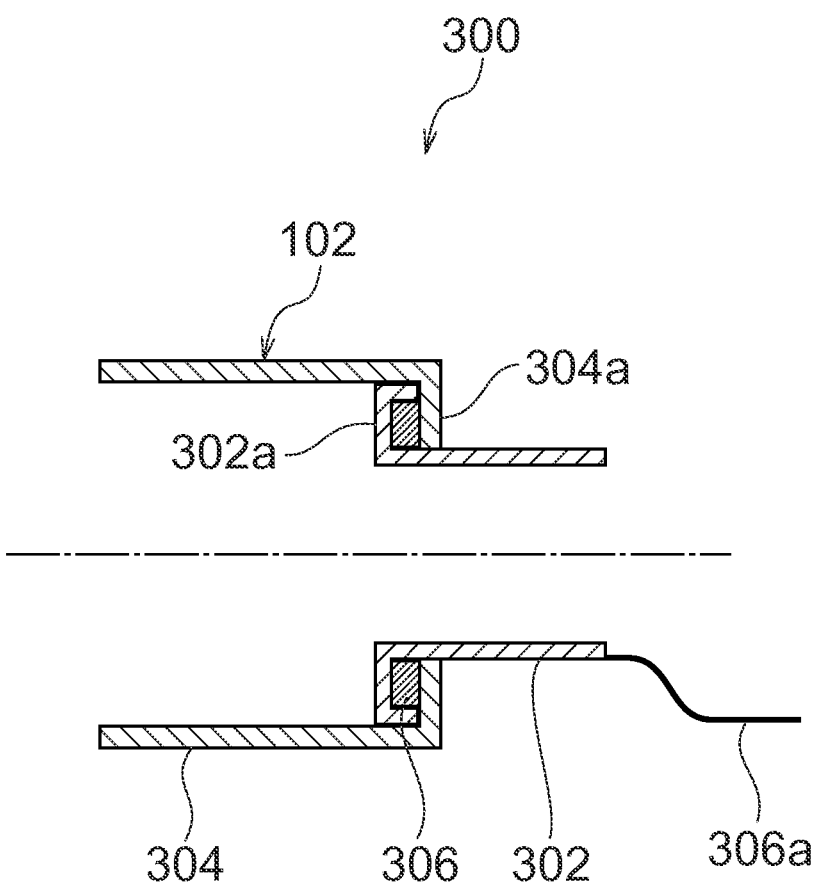
FIG. 15 is a sectional view of the hood in the fifth embodiment.

As illustrated in an exploded view in FIG. 14 and a sectional view in FIG. 15, between the first body part 302 and the second body part 304, an ultrasonic motor 306 is disposed as a rotation device constituting a switching device. In other words, a protrusion 302a protruding toward radially outside is provided at a distal end of the first body part 302, and a protrusion 304a protruding toward radially inside is provided on a proximal end side of the second body part 304. Further, these protrusions 302a and 304a are rotatably coupled with each other via the ultrasonic motor 306.

In this configuration, when the ultrasonic motor 306 is driven by giving the ultrasonic motor 306 a driving signal via an electric cable 306a from an unillustrated control device, the ultrasonic motor 306 rotates the second body part 304 around the axis of the hood body 102 relative to the first body part 302 according to the drive of the ultrasonic motor 306. Thus, the eaves-shaped part 106 rotates around the axis of the hood body 102, and switches between the first state in which the eaves-shaped part 106 is situated inside the observation field range of the observation window 44 and the second state in which the eaves-shaped part 106 is situated outside the observation field range of the observation window 44.

Figure 16:
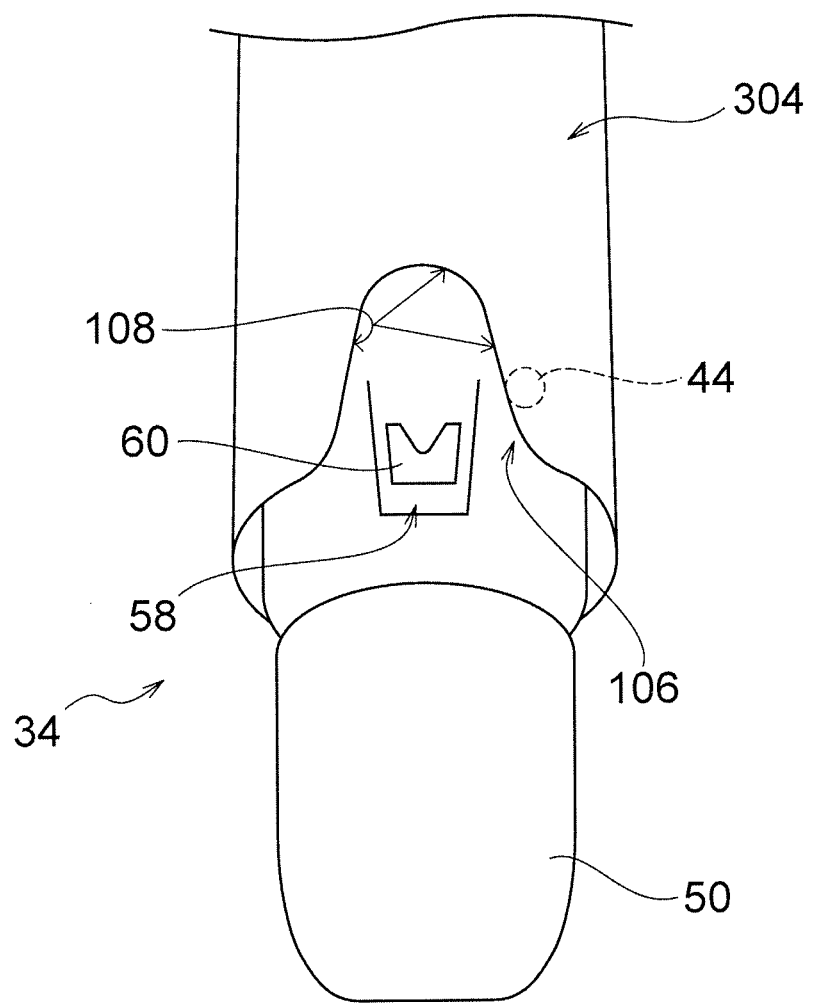
FIG. 16 is a diagram of a first state of the hood in the fifth embodiment.
Figure 17:
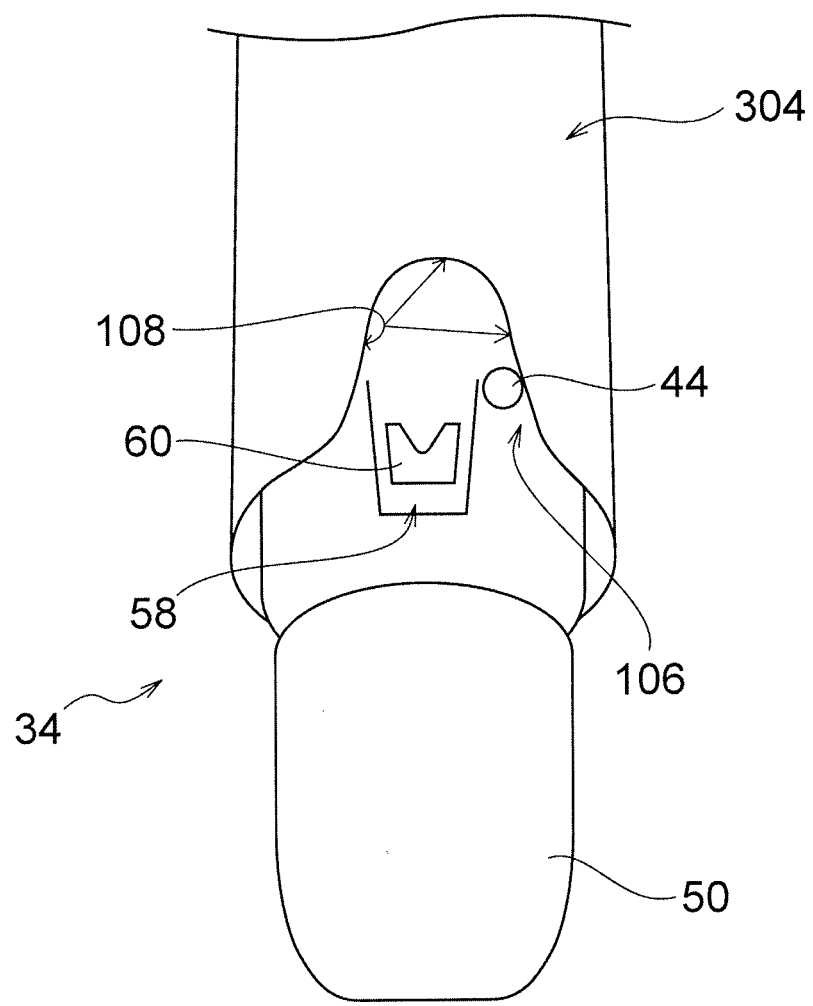
FIG. 17 is a diagram of a second state of the hood in the fifth embodiment.

As illustrated in FIG. 16, in the first state, the eaves-shaped part 106 is arranged in front of the observation window 44, and the notch 108 is arranged at a position where lead-out of the treatment instrument from the treatment instrument lead-out port 58 is not blocked. On the other hand, as illustrated in FIG. 17, in the second state, the eaves-shaped part 106 is retreated from the front of the observation window 44, and the notch 108 is arranged at a position where the lead-out of the treatment instrument from the treatment instrument lead-out port 58 is not blocked.

Therefore, when the visual range of the observation window 44 has priority, the eaves-shaped part 106 can be made in the second state so that the eaves-shaped part 106 is not reflected in the observation field range of the observation window 44.

Next, a hood for an ultrasonic endoscope 350 (hereinafter simply called a hood 350) in a sixth embodiment will be explained.

Figure 18:
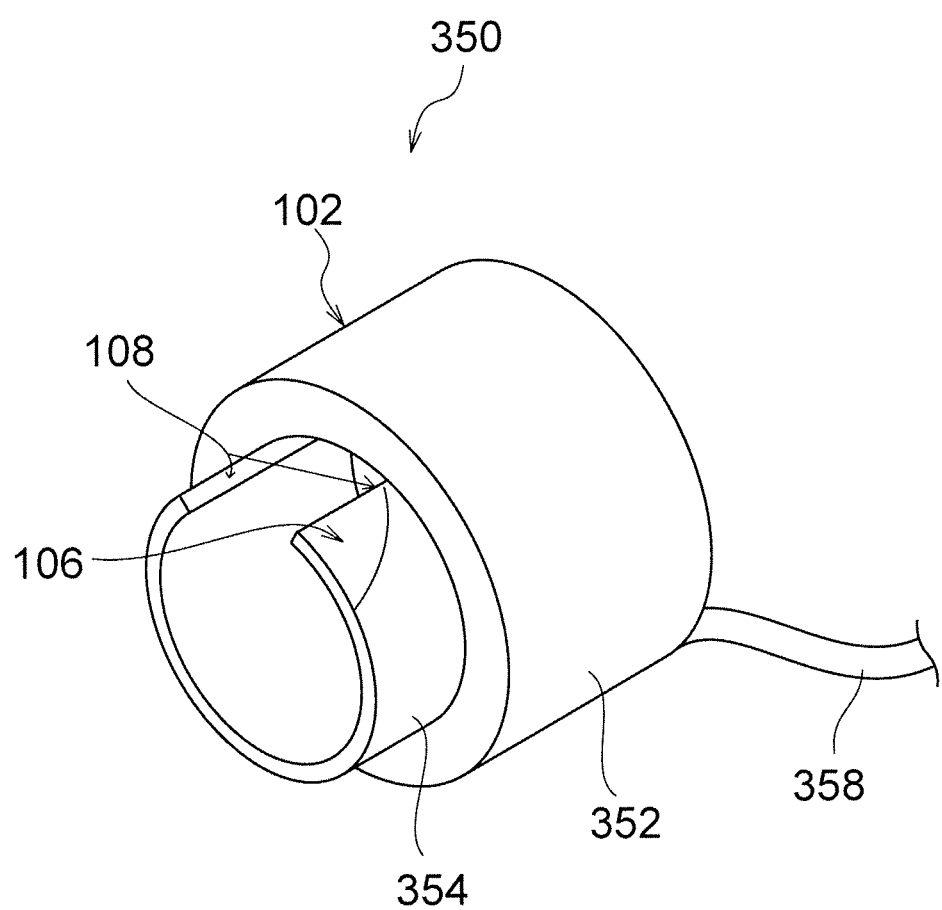
FIG. 18 is a perspective view of a hood in a sixth embodiment.

FIG. 18 is a perspective view illustrating the hood 350 in the sixth embodiment. Additionally, the same part as or a similar function part to the hood 100 in the first embodiment is given the same reference numeral and its explanation will be omitted.

As illustrated in the figure, in the hood 350 in the sixth embodiment, the hood body 102 includes a first body part 352 provided on a proximal end side thereof and a second body part 354 provided on a distal end side of the first body part 352. The second body part 354 is provided with the notch 108 and includes the eaves-shaped part 106. The first body part 352 is to be attached to the distal end part 34.

Figure 19:
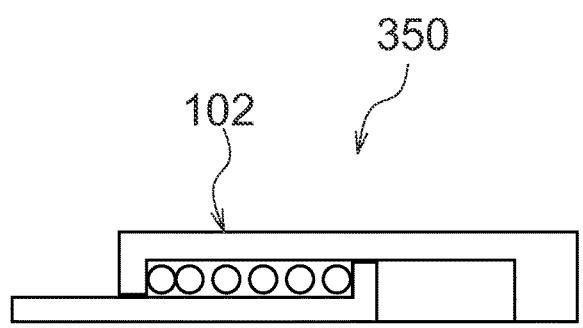
FIG. 19 is a sectional view of the hood in the sixth embodiment.
Figure 19:
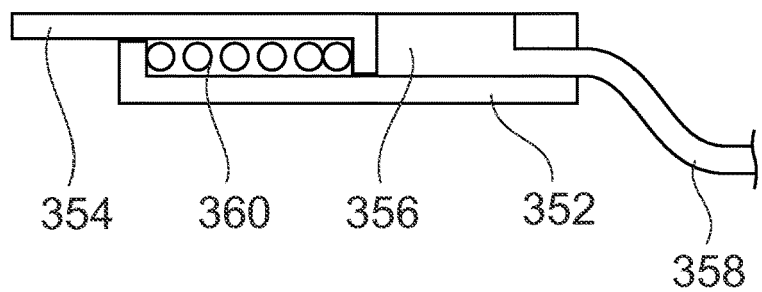
Figure 20:
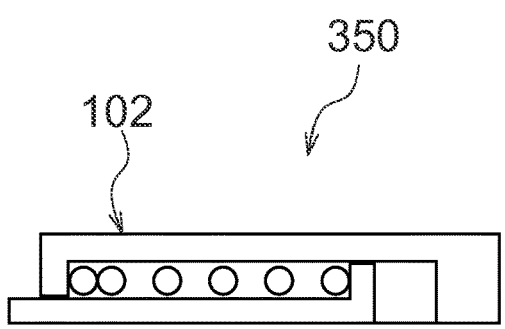
FIG. 20 is a sectional view of the hood in the sixth embodiment.
Figure 20:
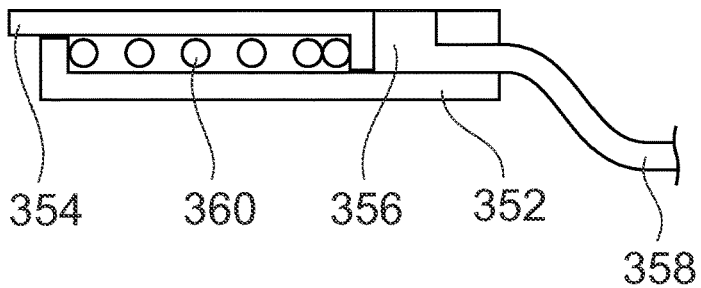

As illustrated in sectional views in FIGS. 19 and 20, the second body part 354 is coupled with the inner circumference side of the first body part 352 movably in the axis direction of the hood body 102, and a fluid storage chamber 356 is provided between the first body part 352 and the second body part 354, as a transferring device constituting a switching device. Then, the fluid storage chamber 356 is connected with an unillustrated fluid outflow and inflow device via a fluid supply tube 358. Additionally, the second body part 354 is urged toward the distal end side or the proximal end side relative to the first body part 352 by a spring 360.

In this configuration, when the fluid outflow and inflow device supplies a fluid (gas or liquid) to the fluid storage chamber 356 to inflate the fluid storage chamber 356, the second body part 354 moves to the distal end side in the axis direction of the hood body 102 relative to the first body part 352. Thus, the state shifts to the first state in which the eaves-shaped part 106 is situated inside the observation field range of the observation window 44 as in FIG. 19.

In contrast, when the fluid outflow and inflow device discharges the fluid from the fluid storage chamber 356 to deflate the fluid storage chamber 356, the second body part 354 moves to the proximal end side in the axis direction of the hood body 102 relative to the first body part 352. Thus, the state shifts to the second state in which the eaves-shaped part 106 is situated outside the observation field range of the observation window 44 as in FIG. 20.

Figure 21:
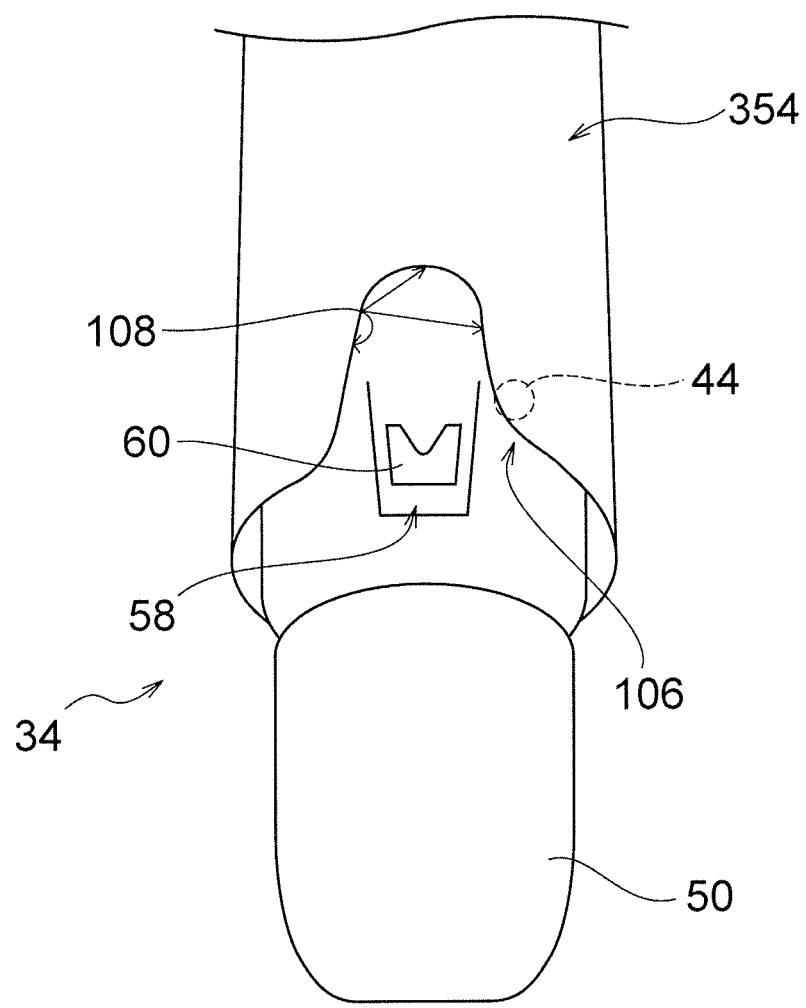
FIG. 21 is a diagram of a first state of the hood in the sixth embodiment.
Figure 22:
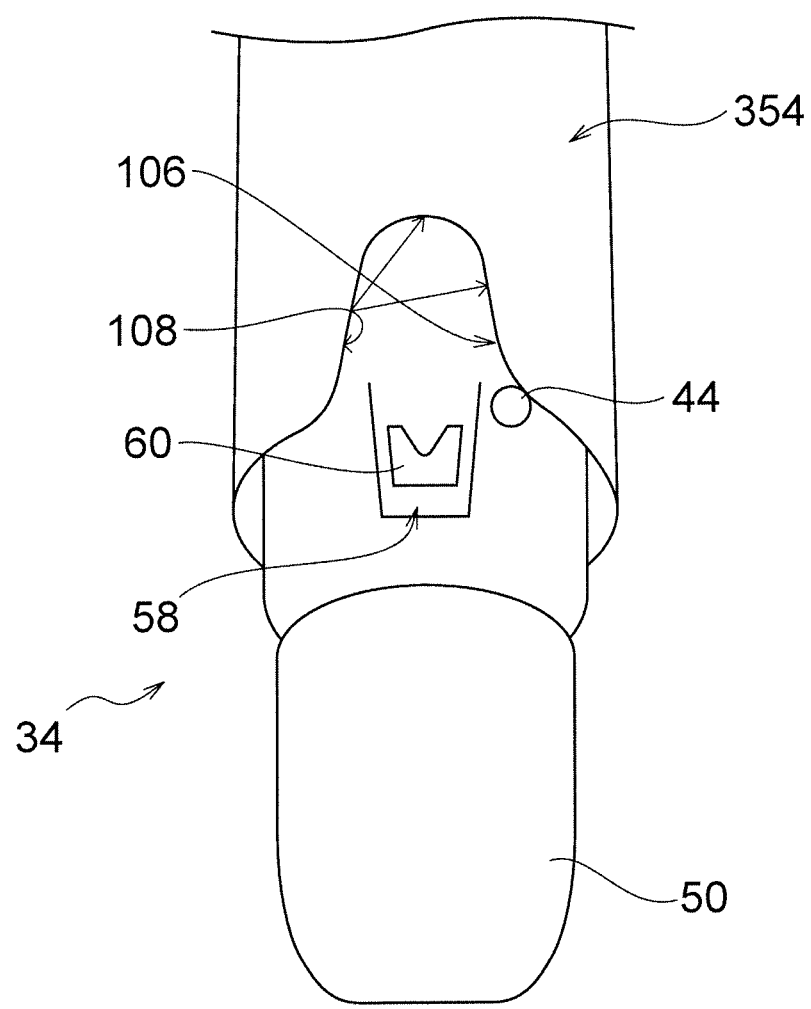
FIG. 22 is a diagram of a second state of the hood in the sixth embodiment.

As illustrated in FIG. 21, in the first state, the eaves-shaped part 106 is arranged in front of the observation window 44, and the notch 108 is arranged at a position where lead-out of the treatment instrument from the treatment instrument lead-out port 58 is not blocked. On the other hand, as illustrated in FIG. 22, in the second state, the eaves-shaped part 106 has retreated from the front of the observation window 44, and the notch 108 is arranged at a position where lead-out of the treatment instrument from the treatment instrument lead-out port 58 is not blocked.

Therefore, when the visual range of the observation window 44 has priority, the eaves-shaped part 106 can be made in the second state so that the eaves-shaped part 106 is not reflected in the observation field range of the observation window 44.

Additionally, the spring 360 illustrated in FIGS. 19 and 20 may be a spring that functions as a compression spring urging the second body part 354 toward the proximal end side relative to the first body part 352, in a direction to shift the eaves-shaped part 106 from the first state to the second state. Or, the spring 360 may be a spring that functions as a tension spring urging the second body part 354 toward the distal end side relative to the first body part 352, in a direction to shift the eaves-shaped part 106 from the second state to the first state.

In addition, it is desirable that the eaves-shaped part 106 is given a habit of moving toward radially inside.

What is claimed is:

1. An ultrasonic endoscope comprising:
   an insertion part including a flexible part, a bending part, and a distal end part;
   an ultrasonic transducer disposed at the distal end part of the insertion part and including a plurality of ultrasonic vibrators;

an observation window disposed at the distal end part of the insertion part, the observation window having a slant angle relative to an axis of a longitudinal direction of the insertion part and slanting towards an ultrasonic observation range of the ultrasonic transducer, the observation window having the ultrasonic observation range of the ultrasonic transducer;

a treatment instrument lead-out port disposed on a proximal end side relative to the ultrasonic transducer at the distal end part of the insertion part and at a position adjacent to the observation window;

a hood attached to the distal end part of the insertion part, the hood having a cylindrically shaped hood body that defines a notch integrally provided at a distal end of the hood body at a position overlapping with the treatment instrument lead-out port of the distal end part of the insertion part, and the hood body including a first portion provided at a distal end side part of the notch and protruding toward a front of the observation window; and a switching device, including one of a string member, a balloon, and a motor, wherein the switching device is configured to switch between a first state in which the notch is positioned outside the observation range of the observation window, and a second state in which the notch is positioned inside the observation range of the observation window.

2. The ultrasonic endoscope according to claim 1, wherein the first portion of the hood body is formed using a frame member protruding toward the front of the observation window.

3. The ultrasonic endoscope according to claim 1, wherein the first portion of the hood body is composed of a transparent member.

4. The ultrasonic endoscope according to claim 3, wherein the transparent member is made of silicone rubber or fluorocarbon rubber.

5. The ultrasonic endoscope according to claim 1, wherein:
the first portion of the hood body is urged to a state of shifting from one state to another state of the first state and the second state,
the switching device includes a string member whose one end is coupled with the first portion of the hood body, and
the switching device sets the first portion of the hood body to the another state by applying a tensile force to another end of the string member, and sets the first portion of the hood body to the one state by removing the tensile force from the another end of the string member.

6. The hood for an ultrasonic endoscope according to claim 1, further comprising:
a balloon integrally disposed between the first portion of the hood body and the distal end of the hood body, and
a fluid supply and discharge tube connected to the balloon at one end and configured to supply fluid to the balloon.

7. The hood for an ultrasonic endoscope according to claim 1, wherein
the hood body includes a first body part provided on a proximal end side of the hood body and a second body part provided on a distal end side of the first body part, and
the switching device includes a motor configured to rotate the second body part around an axis of the hood body relative to the first body part, and switches the first portion of the hood body to the first state or the second state by rotating the second body part.

8. An ultrasonic endoscope comprising:
an insertion part including a flexible part, a bending part, and a distal end part;
an ultrasonic transducer disposed at the distal end part of the insertion part and including a plurality of ultrasonic vibrators;
an observation window disposed at the distal end part of the insertion part, the observation window having a slant angle relative to an axis of a longitudinal direction of the insertion part and slanting towards an ultrasonic observation range of the ultrasonic transducer, the observation window having the ultrasonic observation range of the ultrasonic transducer;
a treatment instrument lead-out port disposed on a proximal end side relative to the ultrasonic transducer at the distal end part of the insertion part and at a position adjacent to the observation window;
a hood attached to the distal end part of the insertion part, the hood having a cylindrically shaped hood body that defines a notch integrally provided at a distal end of the hood body at a position overlapping with the treatment instrument lead-out port of the distal end part of the insertion part, and the hood body including a first portion provided at a distal end side part of the notch and protruding toward a front of the observation window; and
a switching device configured to switch between a first state in which the notch is positioned outside the observation range of the observation window, and a second state in which the notch is positioned inside the observation range of the observation window, wherein:
the hood body includes a first body part provided on a proximal end side of the hood body and a second body part provided on a distal end side of the first body part, and
the switching device includes a spring, an inflatable fluid storage chamber, a fluid supply and discharge tube that supplies fluid to the inflatable fluid storage chamber, a first body part of the switching device, and a second body part of the switching device, wherein
the second body part of the switching device is coupled with an inner circumference side of the first body part of the switching device and movable in an axis direction of the hood body,
the inflatable fluid storage chamber is provided between the first body part of the switching device and the second body part of the switching device,
the second body part of the switching device is urged toward a distal end side or the proximal end side relative to the first body part of the switching device by the spring, and
the switching device is configured to move the second body part of the switching device along the axis direction of the hood body relative to the first body part of the switching device, and switches the first portion of the hood body to the first state or the second state by moving the second body part of the switching device based on the state of the inflatable fluid storage chamber.

9. The ultrasonic endoscope according to claim 8, wherein the first portion of the hood body is formed using a frame member protruding toward the front of the observation window.

10. The ultrasonic endoscope according to claim 8, wherein the first portion of the hood body is composed of a transparent member.

11. The ultrasonic endoscope according to claim 10, wherein the transparent member is made of silicone rubber or fluorocarbon rubber.

* * * * *